United States Patent
Prasad et al.

(10) Patent No.: US 11,426,152 B2
(45) Date of Patent: Aug. 30, 2022

(54) MULTILEVEL LATERAL ACCESS SYSTEM

(71) Applicant: SPINE WAVE, INC., Shelton, CT (US)

(72) Inventors: Srinivas Prasad, Haverford, PA (US);
Jordan Holder, Monroe, NY (US)

(73) Assignee: SPINE WAVE, INC., Shelton, CT (US)

( * ) Notice: Subject to any disclaimer, the term of this patent is extended or adjusted under 35 U.S.C. 154(b) by 113 days.

(21) Appl. No.: 16/775,364

(22) Filed: Jan. 29, 2020

(65) Prior Publication Data
US 2020/0237358 A1    Jul. 30, 2020

Related U.S. Application Data

(60) Provisional application No. 62/798,558, filed on Jan. 30, 2019.

(51) Int. Cl.
*A61B 17/02* (2006.01)
*A61B 90/00* (2016.01)

(52) U.S. Cl.
CPC ........ *A61B 17/025* (2013.01); *A61B 17/0206* (2013.01); *A61B 17/0218* (2013.01); *A61B 90/36* (2016.02); *A61B 2017/0256* (2013.01); *A61B 2090/376* (2016.02)

(58) Field of Classification Search
CPC ... A61B 17/02; A61B 17/025; A61B 17/0206; A61B 17/0218; A61B 90/36
See application file for complete search history.

(56) References Cited

U.S. PATENT DOCUMENTS

| | | | |
|---|---|---|---|
| 8,568,306 B2* | 10/2013 | Hardenbrook | A61B 17/0218 600/210 |
| 8,795,167 B2 | 8/2014 | Ainsworth et al. | |
| 8,932,360 B2 | 1/2015 | Womble et al. | |
| 9,867,605 B2* | 1/2018 | Adams | A61B 17/0206 |
| 10,045,768 B2 | 8/2018 | Garcia-Bengochea | |
| 2003/0149341 A1* | 8/2003 | Clifton | A61B 17/0206 600/210 |
| 2004/0230191 A1* | 11/2004 | Frey | A61B 17/7082 606/57 |
| 2013/0225935 A1* | 8/2013 | Nunley | A61F 2/4611 600/231 |
| 2017/0325970 A1* | 11/2017 | Abdou | A61F 2/4455 |
| 2019/0083081 A1* | 3/2019 | Ortiz | A61B 17/0206 |

* cited by examiner

*Primary Examiner* — Christopher J Beccia
(74) *Attorney, Agent, or Firm* — Hoffmann & Baron, LLP

(57) ABSTRACT

An access system for spinal surgery through a lateral approach comprises a tissue retractor including a center body supporting a centering guide having an elongate opening defining an alignment axis. A pair of retractor blades are movably supported by the center body one blade each on either side of said the centering guide, each retractor blade having a proximal end and a distal end, the distal ends of each retractor blade being configured for placement adjacent a spinal column of a patient. A plurality of elongate disc anchors is provided, each disc anchor being sized for individual removable receipt through the centering guide opening. Each disc anchor has a length such that the distal end of each disc anchor extends distally beyond the distal ends of the retractor blades when each disc anchor is respectively disposed in the centering guide opening.

15 Claims, 6 Drawing Sheets

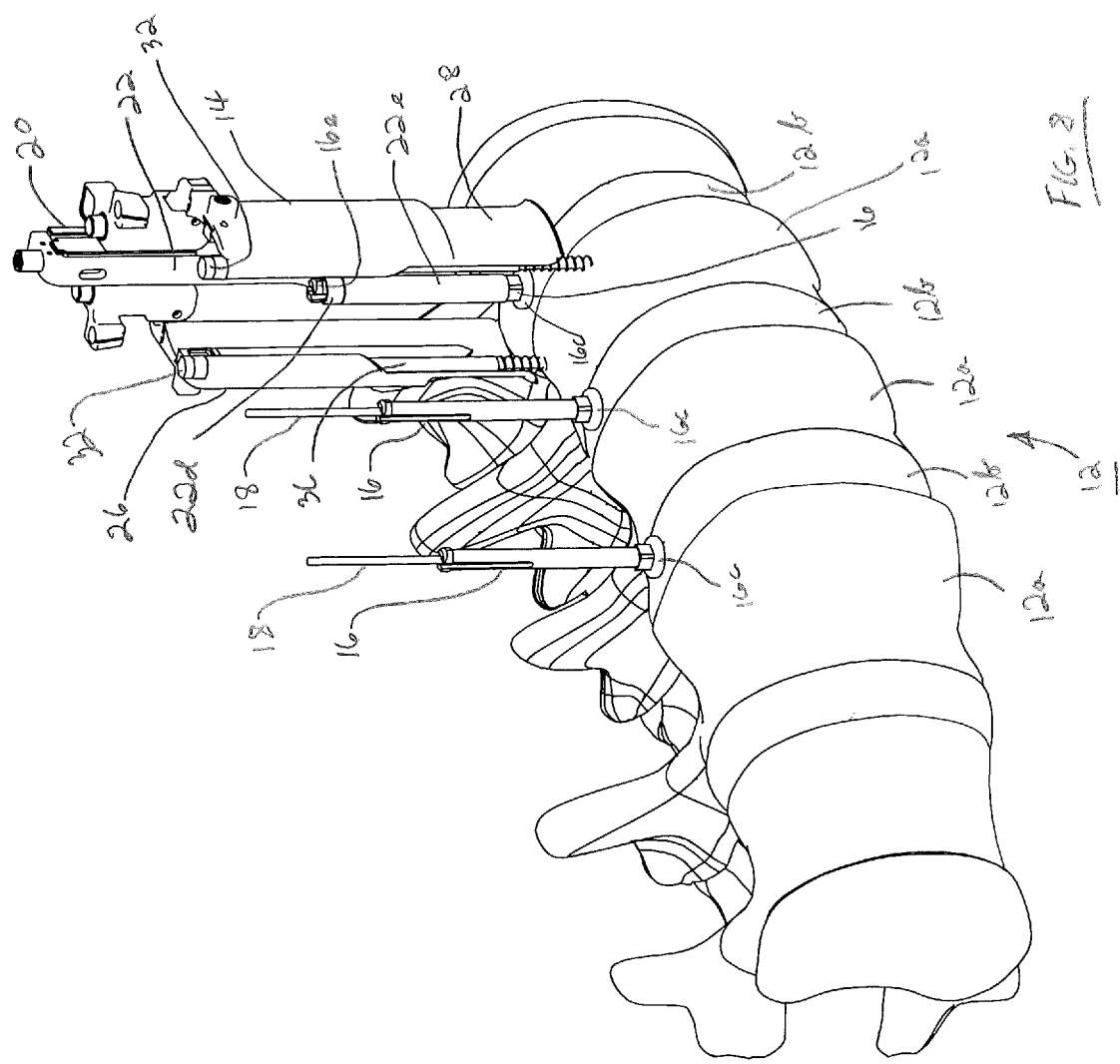

MULTILEVEL LATERAL ACCESS SYSTEM

CROSS-REFERENCE TO RELATED APPLICATION

This application claims priority to U.S. Provisional Patent Application No. 62/798,558, filed Jan. 30, 2019, the entire contents of which are incorporated by reference herein.

FIELD OF THE INVENTION

The subject invention relates to a system and method for accessing a surgical site, and more particularly for accessing multiple levels of a spine in a lateral approach through the psoas muscle.

BACKGROUND OF THE INVENTION

Systems for retracting body tissue and accessing surgical sites are known. In particular, systems are known that provide minimally invasive access to the intervertebral disc space of the lumbar spine using a lateral transpsoas approach that allows direct visualization of the psoas muscle and nerves of the lumbosacral plexus and genitofemoral nerve. Such systems are known as a two-stage retractor system and are described, for example in U.S. Pat. No. 8,568,306, entitled "Surgical Retractor System", issued to Mitchell A. Hardenbrook on Oct. 29, 2013. The retractor is comprised of a primary tubular retractor and a secondary psoas retractor that allow visualization of the psoas muscle by retracting the surrounding tissue and nerves thereby allowing controlled, variable retraction through the psoas muscle and secondary access to the lumbar discs. While providing a significant advance in surgical procedures, such systems do not allow spine surgeons to efficiently perform interbody fusions on multiple levels. The current technique is to treat a disc in its entirety and sequentially move to the next level. This requires repeated alignment using fluoroscopy with these redundant steps increasing operative time. Accordingly, it is desirable to have a system that allows alignment on all the discs to be performed at the same point in the procedure, resulting in significant savings gained in fluoro manipulation/imaging, radiation exposure, and operating time.

SUMMARY OF THE INVENTION

It is an object of the invention to provide an improved system and method for accessing a surgical site. In accordance with a particular aspect, the access system described herein is specifically configured and arranged for spinal surgery through a lateral approach to minimize redundant steps in a multilevel lateral interbody fusion surgery and improve operative efficiency. Such improvement primarily stems from the concept of placing disc anchors in the form of alignment pins in each of the levels to be fused at the same point in time in the procedure to improve the workflow by allowing the steps to be combined. This reduces the amount of time by allowing all fluoroscopy alignment steps to be completed together. Once the disc anchors are set in the operative discs, the psoas muscle can be divided, and a psoas retractor placed. At this point, the tedious alignment steps have been completed and focus is on disc preparation and implant placement.

Accordingly, in one aspect, an access system for spinal surgery through a lateral approach comprises a tissue retractor comprising a center body having a proximal end and a distal end, the center body supporting a centering guide having an elongate opening defining an alignment axis. A pair of retractor blades are movably supported on the center body, the retractor blades being disposed on either side of the centering guide. Each retractor blade has a proximal end and a distal end, the distal ends of each retractor blade being configured for placement adjacent a spinal column of a patient. The system further includes a plurality of elongate disc anchors, each being of size and dimension for individual receipt one at a time through said centering guide opening. Each disc anchor has a proximal end, a distal end and a length therebetween, the length being of extent such that the distal end of each disc anchor extends distally beyond the distal ends of the retractor blades when each disc anchor is respectively disposed in the centering guide opening.

In another aspect, a method of performing spinal surgery from the lateral approach, comprising the steps of imaging from the lateral approach a portion of a spinal column of a patient. During imaging from the lateral approach, a plurality of disc anchors are aligned, one at a time, with the approximate center of each respective disc between the anterior and posterior edges thereof. Each disc anchor is then placed into the respective discs at the aligned center. The lateral imaging is terminated and tissue adjacent each disc is sequentially retracted by referencing each of the disc anchors individually, one at a time to thereby create separate access paths to each disc. The portion of the spinal column of the patient is then imaged from an anterior-posterior approach. During this imaging a surgical procedure is individually performed on each disc through each separate access path.

Other objects and benefits of the invention will become apparent upon consideration of the following written description taken together with the accompanying figures.

DESCRIPTION OF THE FIGURES

FIG. 8 is a perspective view of the access system of FIG. 1 showing the access system in use on a spinal column from the lateral approach.

DESCRIPTION OF THE EMBODIMENTS

Figure 1:
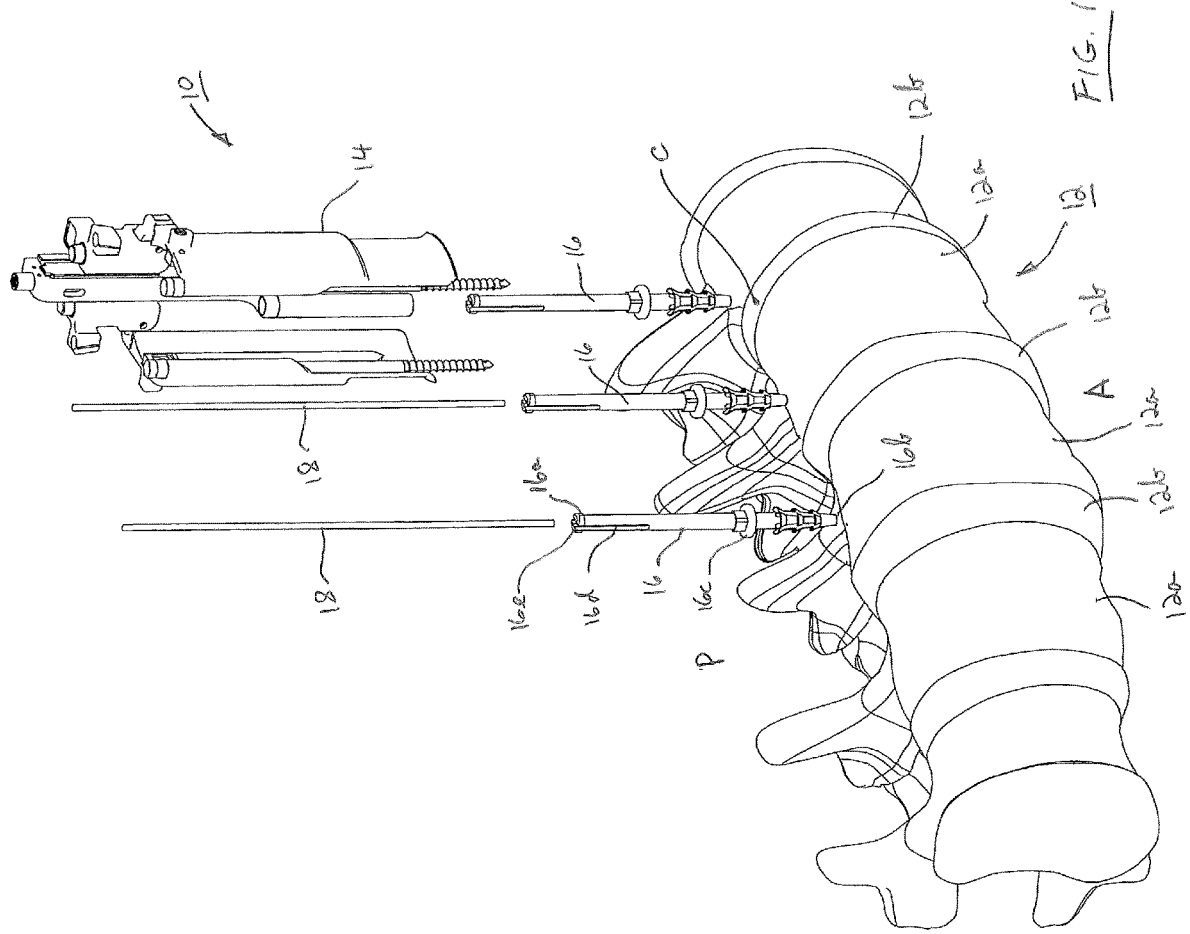
FIG. 1 is a perspective view of an access system in position for use on a spinal column from the lateral approach.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Turning now to FIG. 1 an access system 10 is shown that is specifically configured and arranged for spinal surgery through a lateral approach, particularly for multilevel lateral interbody fusion surgery. Access system 10 is depicted in FIG. 1 as being in position for use on a spinal column 12 from the lateral approach, which is directed along an orientation that is generally orthogonal to the anterior-posterior (A/P) direction of the spinal column 12. As is known, the spinal column 12 consists of a plurality of vertebral bodies 12a each of which is separated by a spinal disc 12b. Access system 10 comprises a tissue retractor 14, a plurality of elongate disc anchors 16, and a plurality of k-wires 18.

Figure 2:
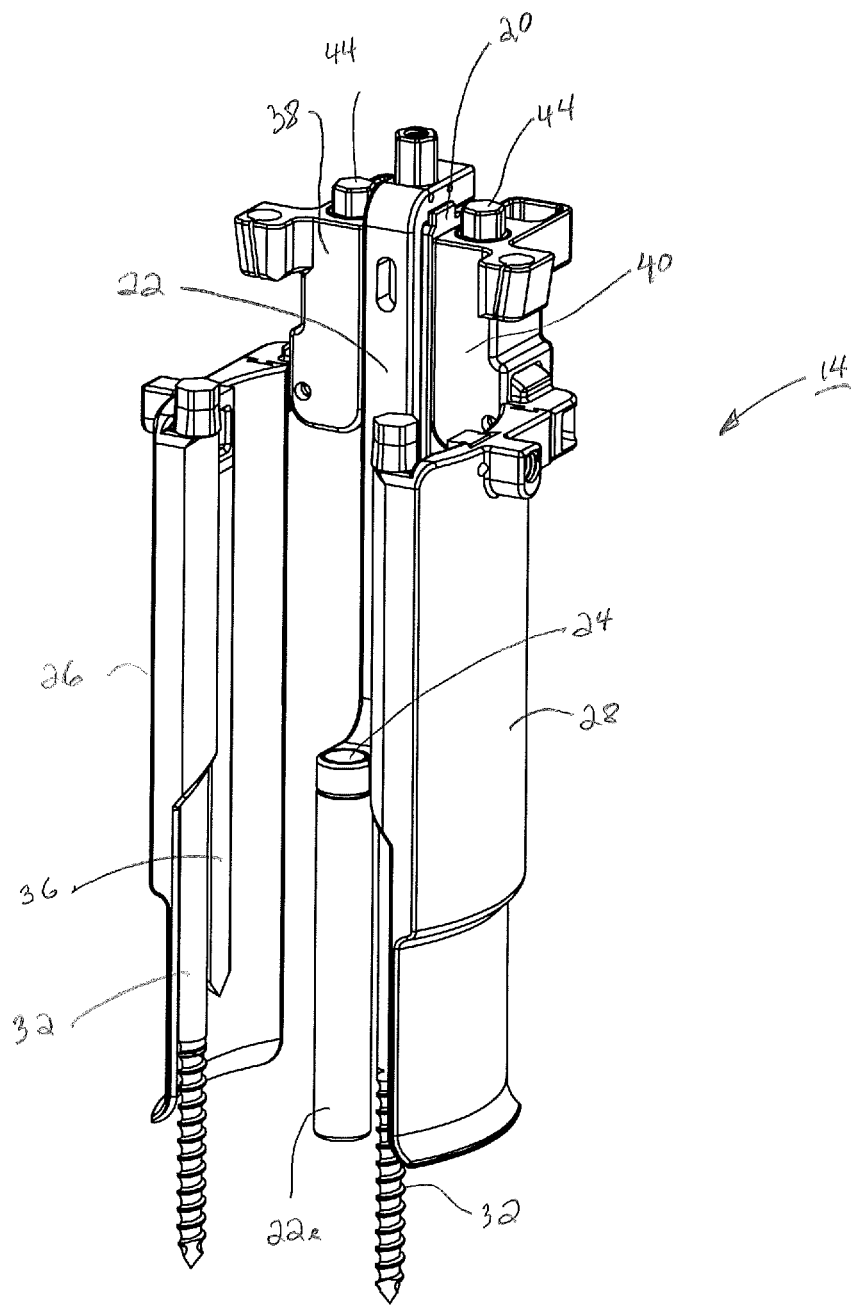
FIG. 2 is a perspective view of the tissue retractor that forms a part of the access system shown in FIG. 1.
Figure 3:
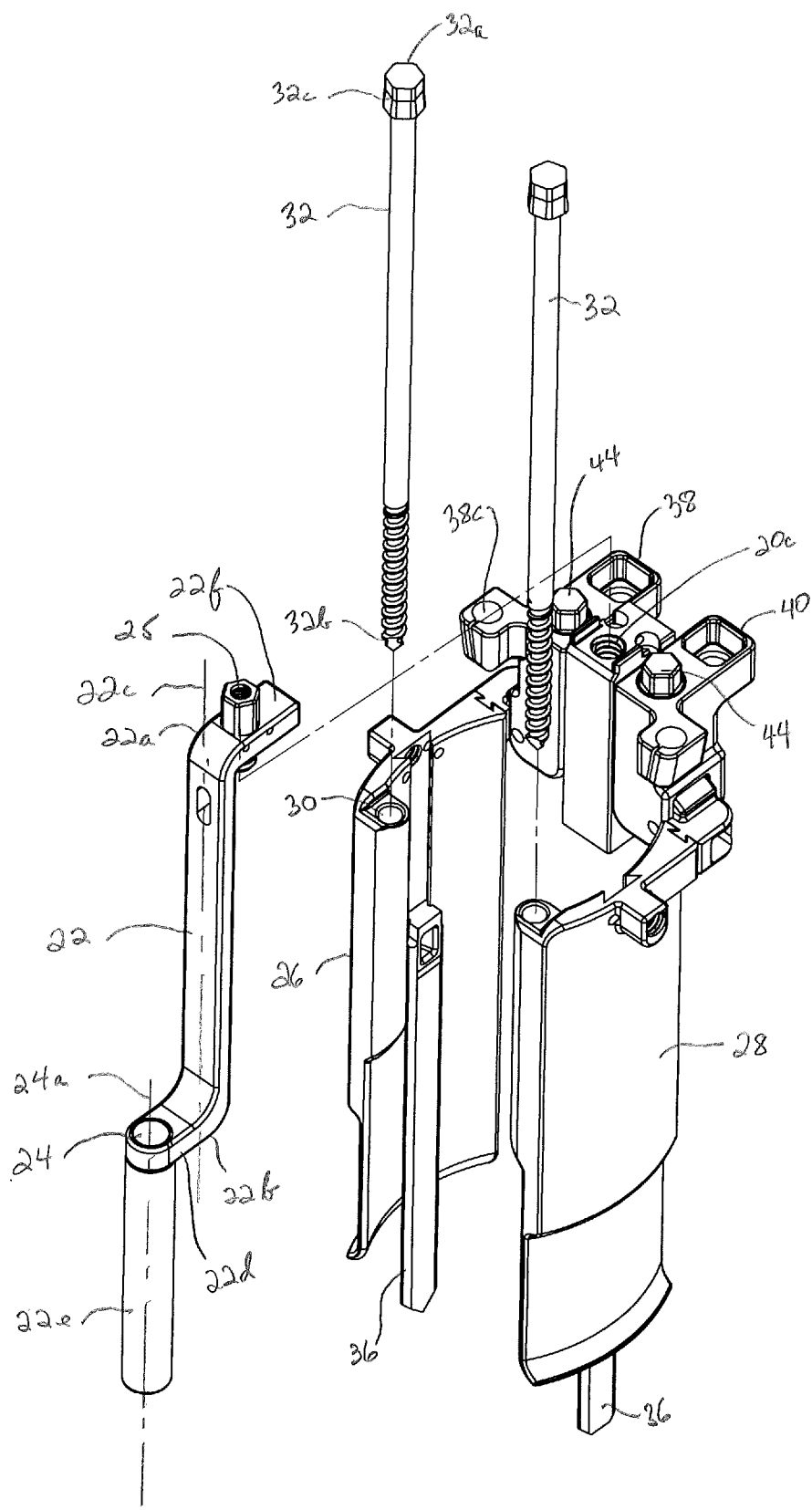
FIG. 3 is an exploded perspective view of the tissue retractor of FIG. 2.
Figure 4:
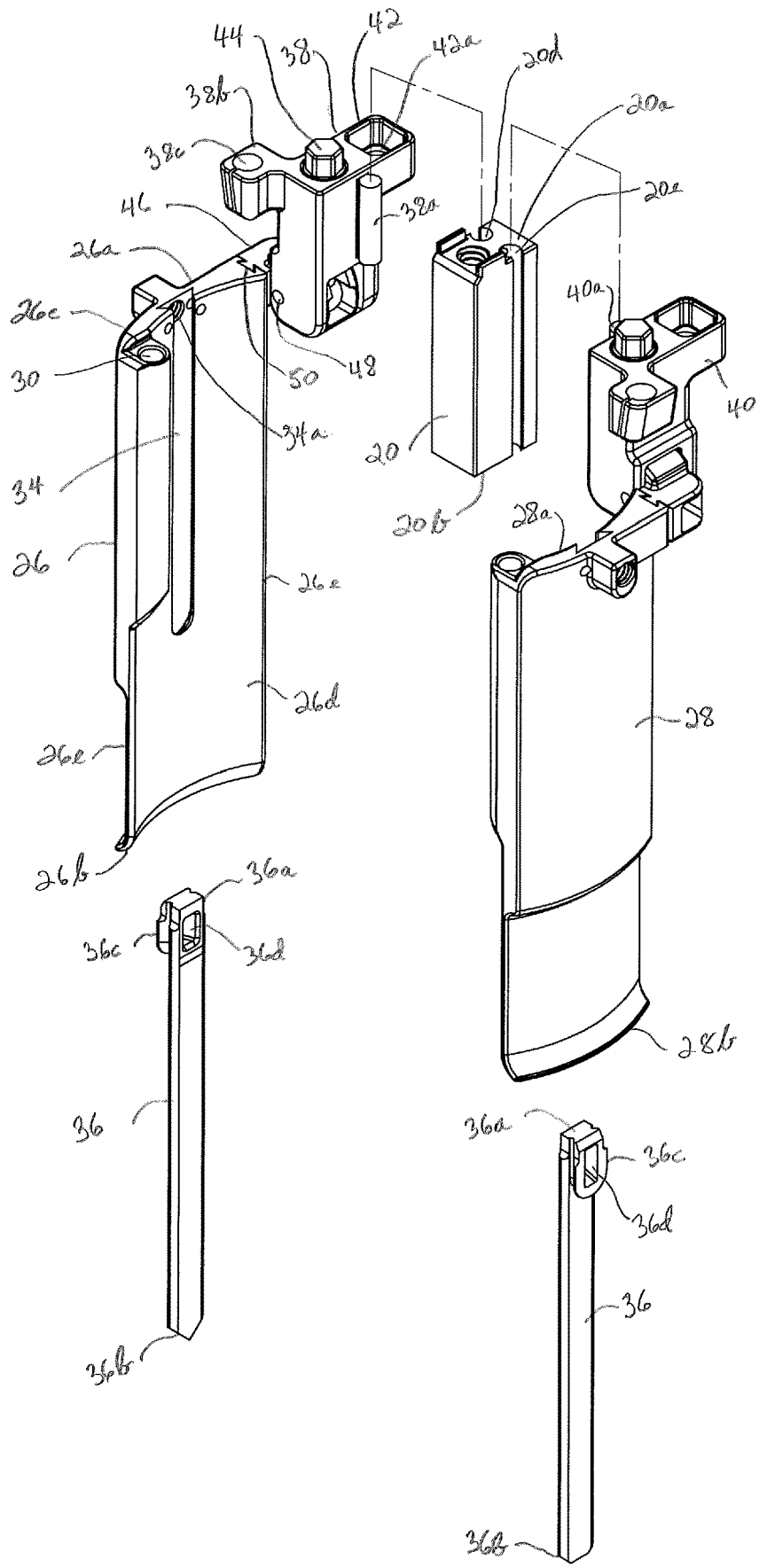
FIG. 4 is an exploded perspective view of a portion of the tissue retractor of FIG. 3 illustrating further details

Referring now to FIGS. 2-4, further details of the access system 10, particularly the tissue distractor 14 are described. Tissue retractor 14 comprises a center body 20 having a proximal end 20a and a distal end 20b. Center body 20 supports a centering guide 22 having an elongated opening 24 defining an alignment axis 24a for individual receipt of a disc anchor 16, as will be described. Tissue retractor 14 further comprises a pair of retractor blades 26 and 28 movably supported on center body 20, retractor blades 26 and 28 being disposed on either side of centering guide 22. The structure of each blade 26, 28 is substantially identical in that each blade 26, 28 is the mirror image of the other. As such, only the details of blade 26 will be described, it being understood that the details of blade 28 are substantially the same.

Retractor blade 26 has a proximal end 26a and a distal end 26b, the distal end 26b being configured for placement adjacent spinal column 12 of a patient as will be described. Blade 26 includes an outer convex surface 26c and an inner concave surface 26d. Adjacent one of the elongate edges of blade 26 an elongate opening 30 is provided to extend along a portion of the blade length, opening 30 being sized and configured for receipt of a fixation pin 32, as will be described. Retractor blade 26 further includes an elongated recessed track 34 extending into inner concave surface 26d. Track 34 extends from the proximal end 26a for an extent along inner concave surface 26d toward distal end 26b of blade 26. Track 34 is configured for slidable receipt of an anchor blade 36, as will be described. Track 34 may have a threaded opening 34a for threaded receipt of a ball/spring plunger (not shown) to provide a detent for holding anchor blade 36 in a secured position relative to blade 26.

Each fixation pin 32, as shown in FIG. 3 is elongate having a proximal end 32a and a distal end 32b. Proximal end 32a includes an engagement feature 32c such as a hexagonal surface for engagement with a suitable tool for rotating fixation pin 32. Distal end 32b is threaded for a portion along distal end 32b for threaded penetration and thereby fixation into the cortical bone of a vertebral body 12a spinal column 12. Each anchor blade 36, as shown in FIG. 4 is elongated having a proximal end 36a and a distal end 36b. Proximal and 36a includes a projecting boss 36c that is sized and configured for sliding disposition within blade track 34. An opening 36d may be provided at the proximal end 36a through boss 36c to receive the ball portion of the ball/spring plunger (not shown) projecting through threaded opening 34a of the proximal end of blade track 34. Distal end 36b may be particularly configured for penetration into a spinal disc 12b of spinal column 12.

Centering guide 22, configured for removable support on center body 20, is elongate having a proximal end 22a, a distal end 22b and defining a longitudinal axis 22c therebetween, as shown in FIG. 3. Longitudinal axis 22c is generally parallel to and offset from alignment axis 24a elongate opening 24. Centering guide 22 has a projection 22d at distal end 22b, projection 22d extending generally orthogonal to centering guide axis 22c. A generally tubular portion 22e projects distally from projection 22d, tubular portion 22 defining elongate opening 24. Centering guide 22 has a mounting flange 22f at proximal end 22a, mounting flange 22f extending generally orthogonal to centering guide axis 22c. A threaded fastener 25 is threadably received in threaded opening 20c of center body 20 to removably couple centering guide mounting flange 22f to center guide 20, as illustrated in FIG. 3.

Each blade 26, 28 is pivotally attached to a respective housing 38, 40. The structure of each housing 38, 40 is substantially identical in that each housing 38, 40 is the mirror image of the other. As such, only the details of housing 38 will be described, it being understood that the details of housing 40 are substantially the same. As shown particularly in FIG. 4, housing 38 includes a generally cylindrical projection 38a for sliding movement in a cooperatively configured generally cylindrical opening 20d extending within center body 20. Such sliding movement allows housing 38 with attached blade 26 to be moved in both the proximal and distal directions on center body 20. Suitable stops are provided to retain projection 38a within opening 20d. A similar arrangement is provided for sliding movement of housing 40 relative to center body 20. As such, a housing 40 includes a generally cylindrical projection 40a that likewise slidably moves within a cooperatively configured generally cylindrical opening 20e on center body 20, opposite opening 20d. Retractor blades 26 and 28 are thereby are each able to slide vertically on center body 20 to allow them to independently register against any non-uniform curvature of the vertebral bodies 12a. It should be understood that other structure may be used to effect cooperative sliding movement between center body 20 and housings 38 and 40. Housing 38 further includes a flange 38b defining an opening 38c that is particularly configured for receipt of a light source, such as an optical cable. Housing 38 further includes an extension portion 42 that defines an opening 42a that is particularly configured to receive handles or other instruments that may be used to position tissue retractor 14 in a surgical site and to facilitate movement of housing 38 and thereby blade 26 in the proximal and distal directions. An actuator 44 is supported by housing 38 for causing pivoting movement of blade 26 relative to housing 38 and thereby to center body 20, as will be described.

Figure 6:
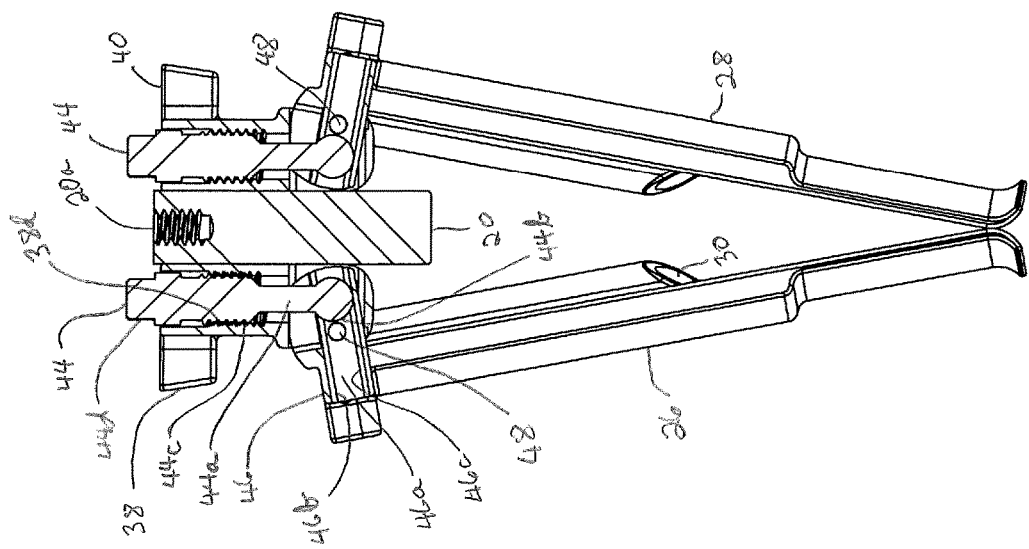
FIG. 6 is the view of the portion of the tissue retractor of FIG. 5 partially cross-sectioned to reveal details of the pivot actuation mechanism.
Figure 5:
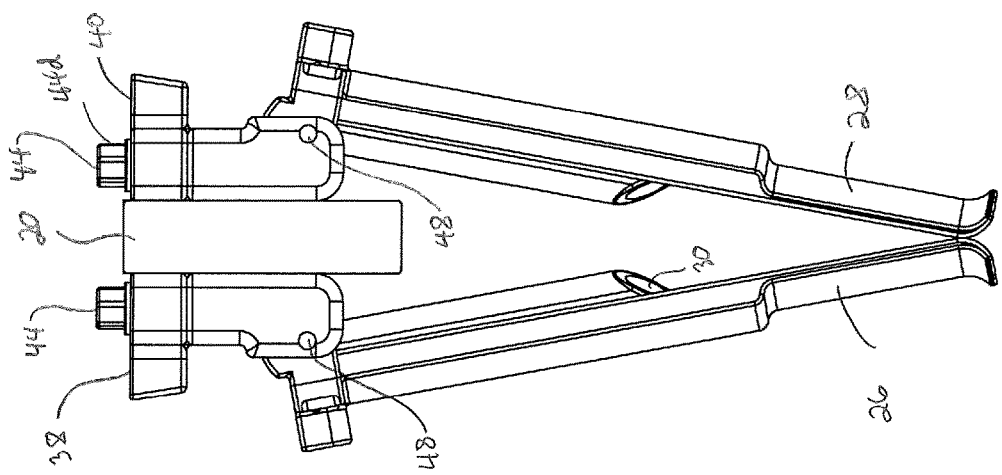
FIG. 5 is a side elevational view of the tissue retractor portion of FIG. 4 showing opposing retractor blades being inclined toward each other in a non-retracted position.
Figure 7:
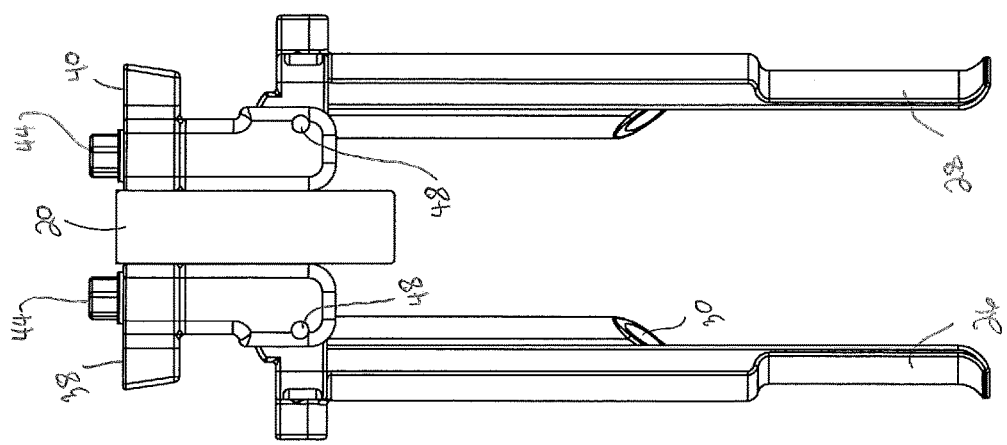
FIG. 7 is a side elevational view of the tissue retractor portion of FIG. 4 showing opposing retractor blades being pivoted away from each other in a retracted position.

Turning also now to FIGS. 5-7, details of the mechanism for pivoting structure blades 26, 28 are described. A pivoting member 46 is pivotally supported within housing 38. Pivoting member 46 is suitably fixedly secured to blade 26 by a dovetail structure 50 (FIG. 4) or other suitable attachment feature. Pivoting member 46 is pivotally coupled to housing 38 by a pivot pin 48 about which pivoting member 46 may toggle. As shown in FIG. 6, pivoting member 46 includes an internal cavity 46a defined by an upper cam surface 46b extending along the proximal side of pivot pin 48 and a lower cam surface 46c extending along the distal side of pivot pin 48. Actuator 44 comprises an elongate post 44a the distal end of which is formed to have a generally spherical surface 44b. A portion of post 44a is formed to have external threads 44c for threadable engagement with internal threads 38d formed within housing 38. The proximal end of post 44a includes an engagement feature 44d such as a hexagonal surface for engagement with a suitable tool for rotating actuator 44. As such, when actuator 44 is rotated in a manner to cause distal movement of post 44a as a result of the threaded engagement of threads 38d and 44c, spherical surface 44b engages lower cam surface 46c thereby pivotably rotating blade 26 about pivot pin 48 until blade 26 reaches the fully retracted position as shown in FIG. 7. When actuator 44 is rotated in an opposite rotational direction to cause proximal movement of post 44a, spherical surface 44b engages upper cam surface 46b thereby pivoting blade 26 about pivot pin 48 until blade 26 reaches the non-retracted position as shown in FIGS. 5 and 6. Thus each blade 26 and 28 can be individually retracted so that the anterior and posterior retraction of tissue, such as the psoas muscle, can be independently adjusted to provide the optimal access to the spinal disc. It should be appreciated that while both blades 26 and 28 are preferably arranged to pivot as described herein, only one of these blades 26 or 28 may be constructed to pivot.

Referring again now to FIG. 1, further details of disc anchors 16 are described. Each disc anchor 16 generally serves as an alignment pin and has a proximal end 16a, a distal end 16b and a length therebetween. Distal end 16b may comprise flexible barbs 16c or other suitable retention features for penetrating a spinal disc 12b and temporarily holding disc anchor 16 therein. Proximally from distal end 16b, disc anchor 16 may include a mechanical stop 16c to limit the depth within which distal end 16b may penetrate spinal disc 12b. Proximal end 16a of disc anchor 16 may have a slot 16d extending through the proximal end 16a distally for a portion of the length of disc anchor 16. A flange 16e may be formed at the proximal end 16a, flange 16e projecting outwardly radially from disc anchor 16. The outer dimension of flange 16e is formed to be greater than the dimension of elongate opening 24 of centering guide 22. Slot 16d allows for an inner radial compression of proximal end 16a as disc anchor 16 is inserted proximally through centering guide opening 24 allowing the compressed portion to snap back to its original position once flange 16e has passed through opening 24, as will be described. After receipt of disc anchor 16 into centering guide opening 24, the length of disc anchor 16 is such that distal end 16b extends distally beyond the distal ends of retractor blades 26 and 28. Disc anchor 16 is cannulated to have a central lumen extending along the length of disc anchor 16 through both the proximal end 16a and the distal end 16b. The central lumen is particularly configured and sized to receive k-wire 18, which is typically an elongate relatively thin metallic pin. While separate disc anchors 16 and k-wires 18 have been described herein, it should be appreciated that in some instances k-wires 18 themselves may serve as disc anchors with opening 24 of centering guide tubular portion 22e being sized and configured to receive k-wires 18 so as to reduce the components of the system 10 and the steps involved in use of system 10.

Having described the structure and function of access system 10 herein, a method of using access system 10 in spinal surgery through a lateral approach, particularly for multilevel lateral interbody fusion is described. More particularly, use of access system 10 and the surgical steps are described, as follows, with particular reference to FIGS. 1 and 8.

1) An incision is made for superficial dissection of the skin and abdominal muscles to create an initial lateral approach access path. That portion of the access path is retracted open using a standard bladed retractor and allows access through the retroperitoneal space (and fat) down to the psoas muscle overlying the anterior aspect of the spinal column 12.

2) Optionally, the peritoneum is retracted using a conventional handheld blade retractor that may or may not attach to the superficial retractor in step 1.

3) A fluoroscopy unit is brought into the field for imaging from the lateral approach to allow the placement and orientation of the disc anchors 16 serving as alignment pins in the disc levels to be treated. The psoas muscle is first dissected under direct visualization. During imaging from the lateral approach, a k-wire 18 is aligned with the approximate center, C of a disc between the anterior and posterior edges thereof in the lateral view, as shown in FIG. 1 Once the disc center is located, the k-wire 18 is placed into the disc 12b and a cannulated disc anchor 16 is driven into the disc annulus over the k-wire 18 until stop 16c contacts the outer surface of spinal disc 12b. Once the disc anchor 16 is seated the fluoroscopy unit is moved to the next level where this step in the procedure is repeated. FIG. 1 shows three disc anchors 16. However, the surgeon may place as many disc anchors 16 as needed for the procedure. Placing all of the disc anchors 16 at the same point in the surgery eliminates time wasted bringing the fluoroscopy unit into and out of the surgical field and re-orienting to the patient. Once the disc anchors 16 are placed, the fluoroscopic imaging from the lateral approach is terminated.

4) Tissue retractor 14 is then placed through the dissected psoas muscle in the non-retracted position shown in FIG. 5, whereby retractor blades 26 and 28 are inclined toward each other presenting a tapered structure to facilitate entrance. The tubular portion 22e of centering guide 22 is placed over the disc anchor 16 and k-wire 18 in the first level to be treated. K-wire 18 is then removed. FIG. 8 shows tissue retractor 14 placed over one of the disc anchors 16 at L4/5 level of the lumbar spine. In this view, the psoas muscle is not shown, but would lie directly on top of the spinal column 12. The centering guide 22 on the center body 20 of the tissue retractor 14 allows the retractor 14 to be both centered and anchored on the disc anchor 16. During such placement of tissue retractor 14, proximal end 16a of disc anchor 16 is compressed as flange 16e passes proximally through centering guide opening 24. As flange emerges through opening 24, flange 16e snaps back to its original position and overlies centering guide projection 22d.

5) The retractor blades 26 and 28 are able to slide vertically proximally on the center body 20 to allow them to independently register against the non-uniform curvature of the vertebral body 12a. Each blade 26 and 28 can also be individually retracted so that the anterior and posterior retraction of the psoas muscle can be independently adjusted to provide an optimal access path to the disc in the first level. Actuator 44 is rotated by a suitable tool to cause blades 26 and 28 to pivot about pivot pins 48 to the position shown in FIG. 7 thereby expanding the dissected psoas muscle and creating an access path through retractor 14 to the spinal disc 12b.

6) Slidable blade anchors 36 are included on the retractor blades 26 and 28 to allow further anchorage of the tissue retractor 14 onto the spinal column 12. This allows independent adjustment of the retractor blade heights, while allowing the entire tissue retractor 14 to be oriented and locked to the spinal column 12. Once the tissue retractor 14 is fixed in position, the disc anchor 16 and centering guide 22 are jointly removed to allow access to the disc 12b. Joint removal is facilitated by the disc anchor flange 16e that resides on the proximal surface of centering guide projection 22d. Thus, as centering guide 22 is moved proximally to remove centering guide 22 from tissue retractor 14, disc anchor 16 is also removed as projection 22d pulls up on flange 16e and thereby pulls disc anchor 16 out from spinal disc 12b. An optional threaded fixation pin 32 can also be used to anchor the tissue retractor 14 to the adjacent vertebral body 12a if desired, in addition to or in lieu of blade anchors 36.

7) The fluoroscopy unit is then brought into the field for imaging from the anterior-posterior approach. Under such imaging a discectomy and an interbody fusion cage insertion may then be performed in a conventional manner. Once the cage is inserted into the disc space, the tissue retractor 14 is removed and re-docked over the disc anchor 16 in the next level through the same incision. The above steps 4-7 are repeated until access paths to the discs in all levels have been created and all disc levels have been treated.

While the invention has been illustrated and described in detail in the drawings and foregoing description, the same should be considered as illustrative and not restrictive in character. As such, it is understood that only the preferred embodiments have been presented and that all changes, modifications and further applications that come within the spirit of the invention are desired to be protected.

What is claimed is:

1. An access system for spinal surgery through a lateral approach, comprising:
   a tissue retractor comprising a center body having a proximal end and a distal end, said center body supporting a centering guide having a proximal end, a distal end, and an elongate opening defining an alignment axis, said retractor comprising a pair of retractor blades movably supported on said center body, said retractor blades being disposed on either side of said centering guide, each retractor blade having a proximal end and a distal end, said distal ends of each retractor blade being configured for placement adjacent a spinal column of a patient; and
   a plurality of elongate disc anchors, each being of size and dimension for individual receipt one at a time through said centering guide opening, each disc anchor having a proximal end, a distal end and a length therebetween, the length being of extent such that the distal end of each disc anchor extends distally beyond the distal ends of said retractor blades when said each disc anchor is respectively disposed in the centering guide opening.

2. The access system of claim 1, wherein said retractor blades are configured for sliding in the proximal and distal directions on said center body.

3. The access system of claim 2, wherein at least one of said retractor blades is attached to said center body for pivoting movement relative to said center body.

4. The access system of claim 3, wherein both of said retractor blades are attached to said center body for pivoting movement relative to said center body.

5. The access system of claim 3, wherein an actuator is disposed at said proximal end of said center body for causing pivoting movement of said at least one retractor blade.

6. The access system of claim 5, wherein the attachment of said at least one retractor blade and said center body includes a threaded mechanism actuated by said actuator.

7. The access system of claim 1, wherein said centering guide is removably supported by said center body.

8. The access system of claim 7, wherein said centering guide is elongate having a longitudinal axis, and wherein said centering guide includes a projection at said distal end, said projection having said opening, said alignment axis of said centering guide opening being generally parallel and offset from the longitudinal axis of said center body.

9. The access system of claim 7, wherein each disc anchor is configured to be jointly removable with the removal of said centering guide from said center body.

10. The access system of claim 1, wherein said disc anchors are cannulated with a lumen extending throughout said length of each disc anchor.

11. The access system of claim 10, wherein said system comprises a plurality of k-wires, each k-wire being configured for individual receipt into a respective lumen of said cannulated disc anchors.

12. The access system of claim 1, wherein said system further comprises at least one blade anchor movably attached to one of said retractor blades, said at least one blade anchor having a proximal end and a distal end, said distal end being configured for penetration into a spinal disc.

13. The access system of claim 1, wherein said system further comprises at least one fixation pin supported by at least one of said retractor blades, said at least one fixation pin having a proximal end and a distal end, said distal end being configure for penetration into a vertebral body.

14. The access system of claim 9, wherein said centering guide has a proximal end and a distal end, and wherein the length of each elongate disc anchor is such that the proximal end of each elongate disc anchor extends proximally beyond the proximal end of said centering guide when said each disc anchor is respectively disposed in the centering guide opening.

15. The access system of claim 14, wherein the proximal end of each elongate disc anchor comprises a compressible flange that extends outwardly beyond and overlies the proximal end of said centering guide when said each disc anchor is respectively disposed in the centering guide opening.

* * * * *